United States Patent
Thong

(10) Patent No.: US 6,345,199 B1
(45) Date of Patent: Feb. 5, 2002

(54) IMPLANT CARDIOVERTER, ESPECIALLY DEFIBRILLATOR

(75) Inventor: Tran Thong, Portland, OR (US)

(73) Assignee: Biotronik MeB-und Therapiegeräte GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/407,843

(22) Filed: Sep. 29, 1999

(30) Foreign Application Priority Data

Sep. 29, 1998 (DE) .......................................... 198 44 598

(51) Int. Cl.$^7$ ................................................. A61N 1/36
(52) U.S. Cl. ............................................................. 607/5
(58) Field of Search ............................. 607/5; 600/509, 600/510, 515, 516, 518

(56) References Cited

U.S. PATENT DOCUMENTS

| | | | |
|---|---|---|---|
| 5,312,441 A | * | 5/1994 | Mader et al. |
| 5,348,021 A | | 9/1994 | Adams et al. |
| 5,464,433 A | | 11/1995 | White et al. |
| 5,545,182 A | | 8/1996 | Stotts et al. |
| 5,718,242 A | | 2/1998 | McClure et al. |
| 5,782,876 A | | 7/1998 | Flammang |

FOREIGN PATENT DOCUMENTS

| | | |
|---|---|---|
| EP | 0653224 | 5/1995 |
| EP | 0862928 | 9/1998 |

* cited by examiner

Primary Examiner—Scott M. Getzow
(74) Attorney, Agent, or Firm—Browdy and Neimark

(57) ABSTRACT

An implantable cardioverter, especially defibrillator, having a morphology detector (3) to measure and evaluate EKG signals for the purpose of discriminating between different tachycardia conditions of the heart. The morphology detector (3) having a signal width detector, by which the respective width of the EKG signal between every two successive crossings through the isoelectrical line of the EKG can be measured; a threshold value discriminator to determine whether the EKG signal between two such successive crossings exceeds a defined threshold value; and a comparator for the signal width, coupled to the signal width detector and the threshold value discriminator. The morphology detector compares the respective current signal width value selected by the threshold value discriminator and measures by signal width detector to a pre-set selection parameter to differentiate between two different conditions of tachycardia.

7 Claims, 3 Drawing Sheets

IMPLANT CARDIOVERTER, ESPECIALLY DEFIBRILLATOR

BACKGROUND OF THE INVENTION

1. Technical Field of the Invention

The present invention relates to an implantable cardioverter, especially a defibrillator, with a morphology detector for detection and evaluation of electrocardiogram (EKG) signals for the purpose of discriminating between different tachycardia conditions of the heart.

2. Prior Art

Regarding the background of the invention, it is important to note in principle, that pathological rhythm abnormalities of the heart, so-called "tachycardias," exist as a clinical picture, which can occur either atrial or ventricular, i.e., in the atrium of the heart or in the ventricle. This is a condition of the heart with a pathologically increased heart rate, which can be significantly higher than 100 beats per minute. In this context one generally distinguishes between two different disorder patterns, i.e., the atrial or ventricular fluttering on one hand and the atrial or ventricular fibrillation on the other hand. The "fluttering" is a rapid succession of relatively regular heart actions, during which a certain pumping capacity of the heart still remains available. During the "fibrillation" on the other hand, an asynchronous action of the heart muscle cells is present, by which an effective pumping action is no longer achieved.

Both of the above conditions can have identical rates, however, they can be vastly different in their stability and, therefore, in their consequences for the patient. The two types of disorder, "fluttering" and "fibrillation," therefore, call for different cardiological responses. A modern pacemaker or cardioverter must, therefore, be able to distinguish exactly between conditions of fluttering and conditions of fibrillation, to be able to take the appropriate actions. For this purpose these devices incorporate the above-mentioned morphology detector, which detects and evaluates the EKG signal in a suitable manner. Naturally, a large range of options exists for the actual method by which the signals are processed and translated into action, which are limited primarily by the special location and related conditions of compatibility for a cardioverter or defibrillator.

With respect to the state of the art, it needs to be pointed out that known morphology detectors measure, for instance, the width of the entire depolarization complex of the EKG signal. The measurement of the width of individual spikes does not take place. This is the case, for example, with the detectors according to U.S. Pat. Nos. 5,542,430 and 5,447,519. The morphology detector according to the U.S. Pat. No. 5,560,369 furthermore predominantly addresses an automatic setting of threshold values, but not a discrimination between the tachycardia conditions described above.

With the device for controlling heart arrhythmias presented in the U.S. Pat. No. 5,086,772, it is possible to distinguish, among others, between conditions of a ventricular tachycardia and supraventricular tachycardia. This is done by utilizing the so-called 50% width of the R wave of the EKG signal. A discrimination between "fluttering" and "fibrillation" does not take place.

From EP 0 592 625 B 1 a cardioverter or defibrillator is known that encompasses an electrogram wave form analyzer. The electrical signals from the patient's heart are digitized and stored sequentially. These stored signals are scanned within a certain time window and the gain of the signals is practically determined by subtraction. This serves as the basis for delivery of the appropriate therapy by the cardioverter or defibrillator.

OBJECT AND SUMMARY OF THE INVENTION

The present invention is now based on the object of improving an implantable cardioverter so that its morphology detector can reliably discriminate between different tachycardia conditions of the heart and especially between a "fluttering" and a "fibrillation".

This object is met with an implantable cardioverter with a morphology detector having the following characteristics:

- a signal width detector (10), by which the width (w) of the EKG signal peak between every two successive crossings (d2) through the isoelectric line (7) of the EKG can be determined,
- a threshold value discriminator (11) to determine whether the EKG signal between two such successive crossings (d1, d2) exceeds a defined threshold value (T, a1), and
- a comparator (12) for the signal width (ws), which is coupled to the signal width detector (10) and the threshold value discriminator (11), to compare the current value of the signal width (ws) selected by the threshold value discriminator (11) and determined by the signal width detector (10) to a pre-set selection parameter in order to discriminate between two different conditions of tachycardia.

The present invention makes use of the discovery that during a fluttering condition of the heart, the EKG signal returns to the baseline or isoelectrical zero line and displays small peaks (spikes). During a fibrillation condition of the heart, by contrast, the EKG signal on the average deviates more strongly from the baseline and has significantly wider peaks. This will be explained in more detail later, in connection with the description of the figures.

The morphology detector proposed in accordance with the invention now utilizes the width of the EKG signal between two zero crossings through the baseline in such a way that only those EGK signal peaks are monitored whose amplitude exceeds a defined threshold value. To provide the above functionalities, the above-described signal width detector and the threshold value discriminator act together. With respect to the term "defined threshold value" it should be noted that this does not necessarily have to be a constant threshold value. It may also be a so-called "adaptive threshold value", which is determined dynamically based on a continual evaluation of the EKG signal on the basis of the respective peak amplitude. An adaptive threshold setting of this type, incidentally, is known in the field of cardioverters and is being used in practice.

The comparator for the signal width that is furthermore provided compares the current value of the signal width to a pre-set selection parameter, which separates the tachycardia conditions of "fluttering" and "fibrillation" as reliably as possible. A comparison is, therefore, made whether the determined value of the signal width, which may optionally be processed by means of customary statistical methods and evaluations, exceeds the selection parameter, thus indicating the likelihood that a fibrillation condition (wide peaks) is present, or whether the determined signal width value is lower than the selection parameter, thus indicating a fluttering of the heart, based on the accompanying smaller peaks.

BRIEF DESCRIPTION OF THE DRAWINGS

An embodiment of the invention will, furthermore, be explained in more detail in the following description based on the appended drawings, in which.

DETAILED DESCRIPTION OF THE PREFERRED EMBODIMENT(S) OF THE INVENTION

The fundamental difference between EKG signals during a fluttering of the heart (FIG. 1) and a fibrillation of the heart (FIG. 2) will now be explained based on FIGS. 1 and 2. During the former condition, the peaks 1 of the EKG signal shown in FIG. 1, which exceed a defined adaptive threshold value T, have a small signal width wd or ws. This signal width is defined as the distance of time between two successive crossings of the EKG signal through the baseline or isoelectrical zero line Z of the EKG.

Figure 2:
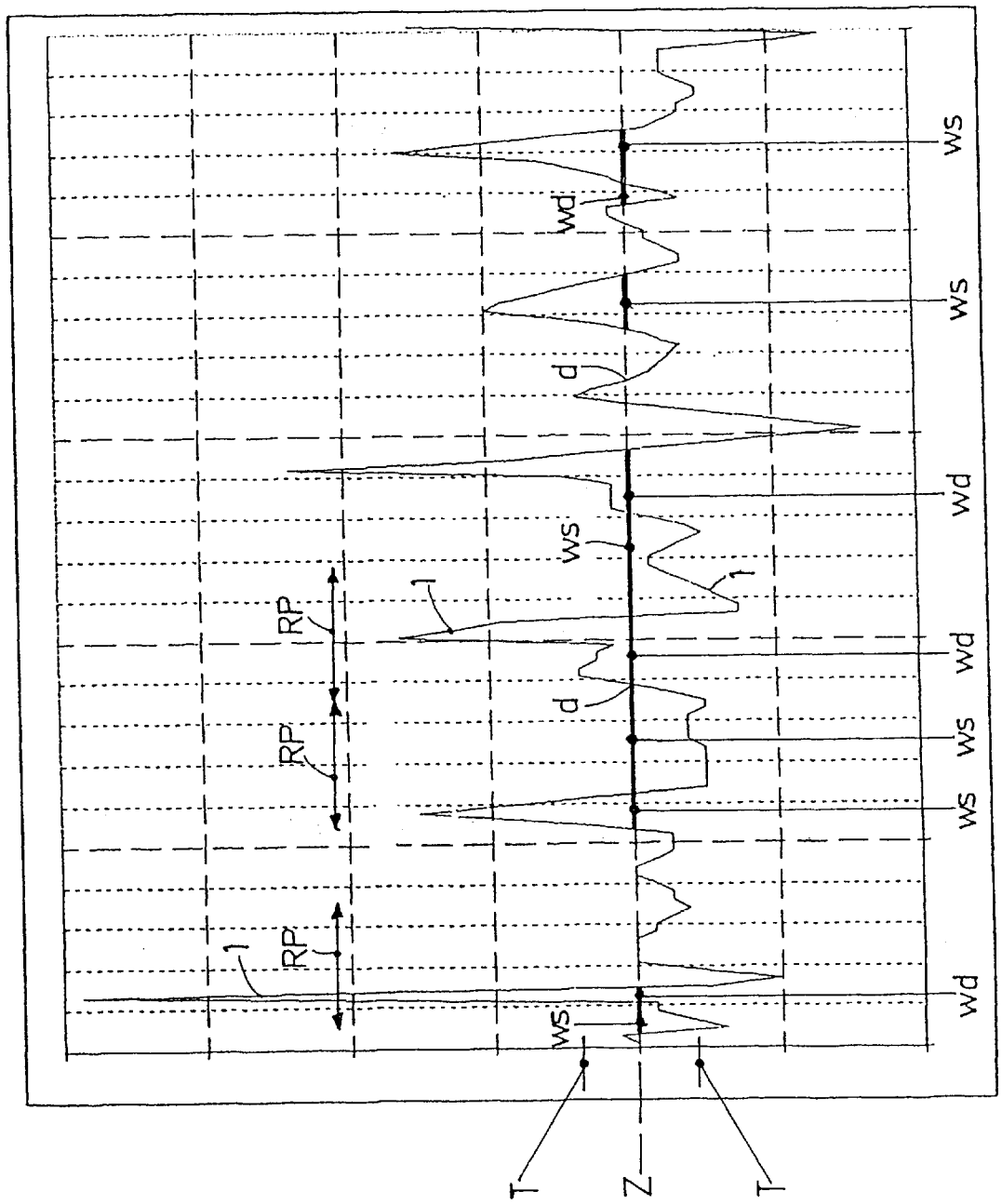
FIG. 2 shows a typical EKG signal curve for the abnormal tachycardia "fibrillation" condition.

In comparison, the signal widths w of the peaks 1 of the EKG signal shown in FIG. 2 are much larger on the average. To this extent the detection, especially of the stored signal widths ws of the peaks 1, may, therefore, be used to differentiate between arrhythmias that are similar in their heart rates.

Figure 1:
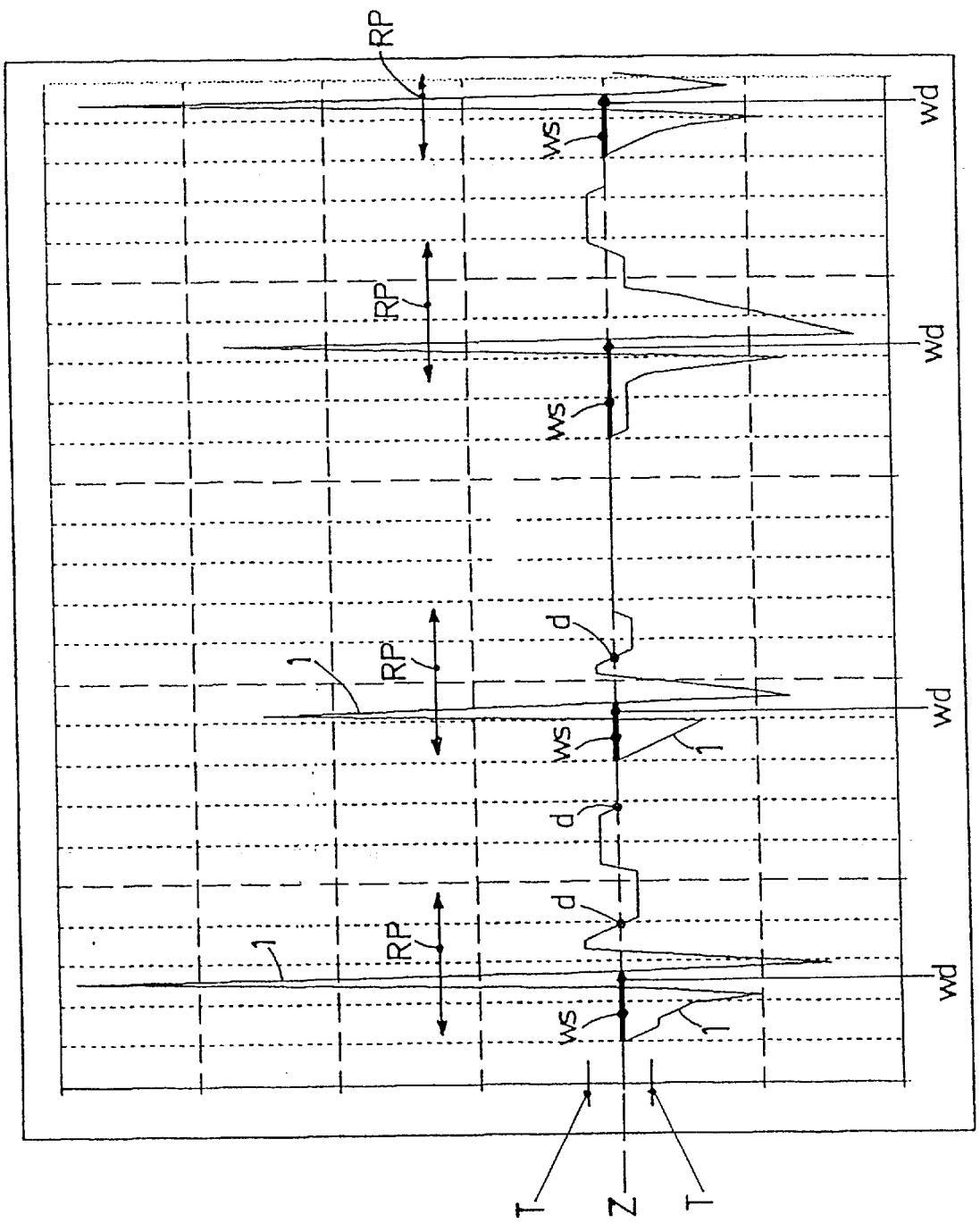
FIG. 1 shows a typical EKG signal curve for the abnormal tachycardia "fluttering" condition.

Regarding the two FIGS. 1 and 2, it needs to be noted in connection with the defined adaptive threshold value T, that this value has been entered into the two drawings as a constant value for reasons of simplicity. However, as has been explained earlier, the threshold value T will change due to the implemented adaption, both over time and especially from refractory period to refractory period and also in between.

Figure 3:
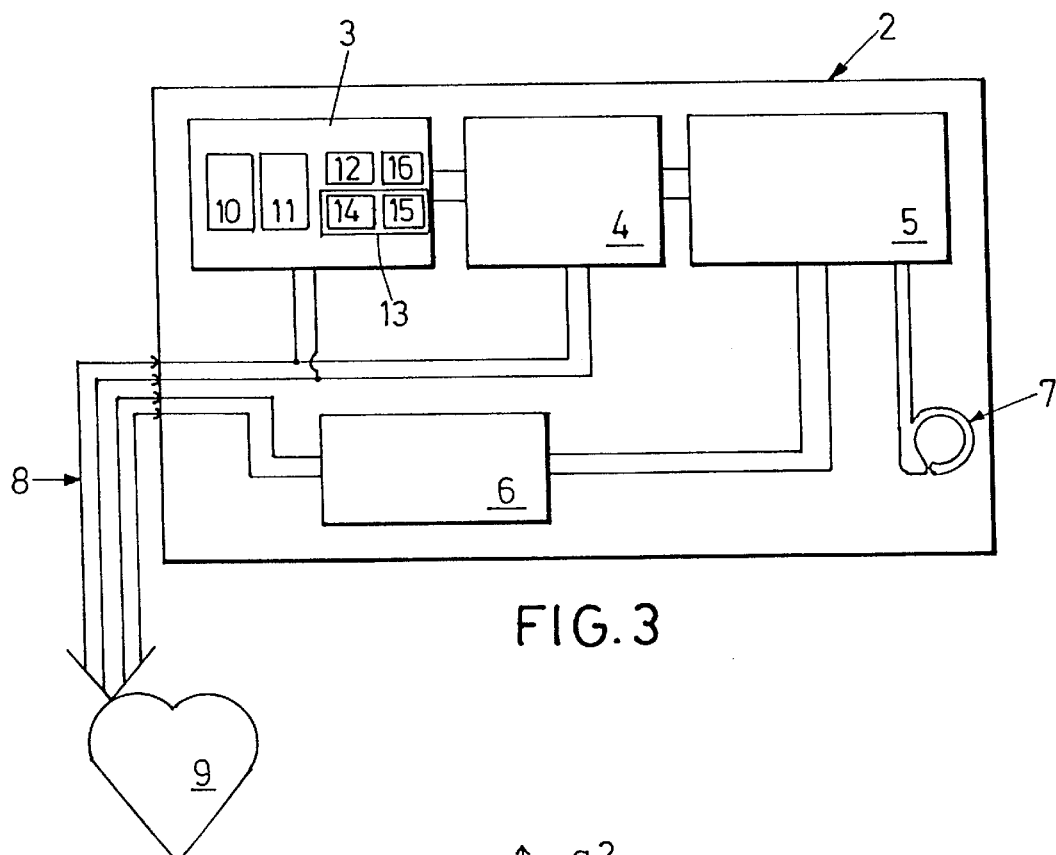
FIG. 3 shows a highly schematic diagram of an implantable cardioverter with morphology detector.

An appropriately equipped implantable cardioverter 2 with an integrated morphology detector 3 for detecting and evaluating EKG signals for the purpose of discriminating between these different types of tachycardia conditions of the heart is presented in a highly schematic illustration in FIG. 3. As is typical for a cardioverter of this type, this cardioverter incorporates further functional components in the form of a heart rate detector 4, a microprocessor-controlled central unit 5 with a central processing unit (CPU) not shown in the drawing, main memory, data memory and program memory, a pulse unit 6 to generate voltage pulses that correspond to the detected heart condition, as well as a telemetry unit 7, by which the cardioverter 1 can be reprogrammed from outside. Via corresponding electrodes 8, which are inserted into the heart or may be applied externally, the cardioverter detects the EKG signals of the heart 9 and emits the above voltage pulses.

Since the general operation principle of cardioverters, defibrillators and pacemakers is commonly known, no further explanations are required regarding the general design of the device shown in FIG. 3.

Further explanation is needed merely regarding the morphology detector 3, which incorporates as functional componentry a signal width detector 10 to determine the signal width w of the EKG signal between two successive crossings through the isoelectrical line Z of the EKG, a threshold value discriminator 11 to determine whether the EKG signal between two such successive crossings exceeds a defined threshold value T, a comparator 12, a maximum-value holding device 13 with a comparing device (14) and memory (15), as well as a peak value indicator 16. The mode of operation of the above units 10 through 16 can be explained with the aid of FIG. 4. As illustrated, the morphology detector 3 detects the EKG signal via its connection shown in FIG. 3 to electrodes 8 that are anchored, for instance, in the atrium of the heart. In the process, the signal width detector 10 detects a crossing d1 of the EKG signal through the zero line Z. The value of the EKG signal subsequently exceeds the threshold value T, with the result that the peak 1.1 is treated as a relevant event. As is apparent from the two curves shown at the bottom of FIG. 4 for the signals ST ("STORE") for the memory 15 and PD ("PEAK DETECT") for the peak value indicator, these two signals are set when the threshold value T is exceeded. The peak-value indicator 16 monitors the course of the peak 1.1 up to its maximum (amplitude a a1), the reaching of which causes the signal PD to be reset. This causes the amplitude value a1 to be read. Since the course of the signal in the peak 1.1 then goes toward the zero line, the "PEAK DETECT" signal PD is not updated at this time. The second zero crossing d2 causes the counter of the signal width detector, which was started by the zero crossing d1, to be read and the signal width w1 of the peak 1.1 to be measured. Since the "STORE" signal ST was furthermore set, the value w1 of the signal width is stored.

During the further course of the signal after the zero crossing w2, the peak value indicator 16 is not updated until the value of the signal exceeds the maximum amplitude value a1 of the peak 1.1 during the course of the peak 1.2. As soon as this is the case, the "PEAK DETECT" signal PD is set again and this peak value is measured when the maximum amplitude value a2 is passed in the peak 1.2. Simultaneously with the setting of the "PEAK DETECT" signal PD, the "STORE" signal ST is again set for the memory 15.

Subsequently, the next zero crossing d3 is registered by the signal width detector 10 and the corresponding signal width w2 is measured. The latter is compared, by the comparing device 14, to the previous value w1 of the signal width that is stored in the memory 15. In the illustrated example in FIG. 4, for instance, the value w2 is, therefore, identified as the maximum value and stored. The maximum values of the individual EKG signals that are obtained in this manner can be compared to a selection parameter, which may, for instance, be pre-set in the central unit 5 in order to discriminate between two different conditions of tachycardia.

Figure 4:
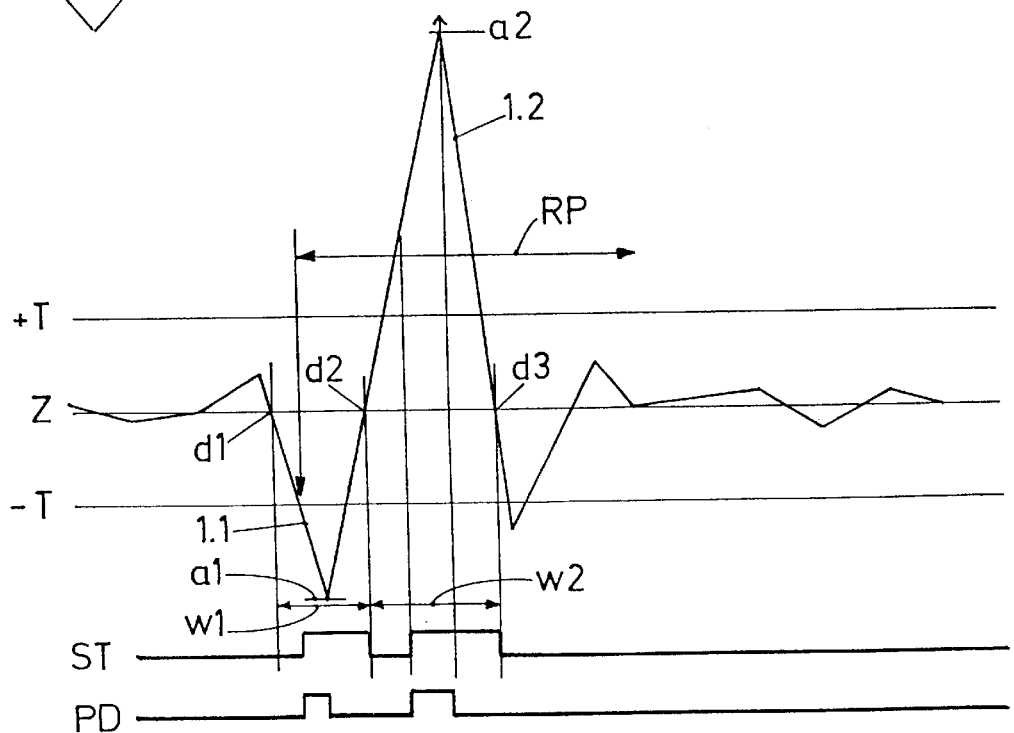
FIG. 4 is a curve diagram to illustrate the principle of operation of the morphology detector.

As can also be discerned from FIG. 4, the morphology detector 3 is designed so that it always detects the EKG signal during the refractory period RP. From experience it is known that this period lasts for roughly 100 ms. Under certain circumstances, for example if large repolarization waveforms (T waves in the ventricle) occur, it is desirable to extend each refractory period. However, since the EKG signal is supposed to be measured only for the depolarization waves (i.e., the P wave and the QRS complex) and not for the repolarization wave, the actual scanning or detection period of the morphology detector can be shortened by deactivation during a predefinable refractory period.

To clarify the detection process of the EKG signal morphology shown by way of example in FIG. 4, detected signal widths (wd) as well as signal widths (ws) that were selected and stored by comparison on the basis of the comparing device 14 have been entered into FIGS. 1 and 2. Likewise, the respective refractory periods RP of the EKG signals have been marked. With a properly selected length of the refractory period, the morphology detector 3 can also detect the width of the signal pulses of the atrial and/or ventricular depolarization wave complex of the EKG signal.

The above functional components of the morphology detector 3 can, of course, be integrated into the central unit 5 and implemented via a control software designed for tachycardia discrimination. It should furthermore be noted that the morphology detector 3, as a secondary detector, is hierarchically subordinate to the heart rate detector 4 of the cardioverter. This means that the morphology detector 3 is invoked to distinguish between a fibrillation and a fluttering of the heart only if a certain heart rate indicating a tachycardia is present.

What is claimed is:

1. An implantable cardioverter, especially defibrillator, with a morphology detector (3) for detection and evaluation of electrocardiogram (EKG) signals for the purpose of discriminating between different tachycardia conditions of the heart, said morphology detector (3) comprising:

a signal width detector (10), by which a width (w) of an EKG signal peak between every two successive crossings (d2) through an isoelectrical line (7) of the EKG can be measured, a threshold value discriminator (11) to determine whether the EKG signal between two said successive crossings (d1, d2) exceeds a defined threshold value (T, a1), and a comparator (12) for the signal width (ws), coupled to the signal width detector (10) and the threshold value discriminator (11), which compares the respective current value (w) of the signal width selected by the threshold value discriminator (11) and measured by the signal width detector (10) to a predetermined selection parameter for the purpose of discriminating between two different tachycardia conditions.

2. A cardioverter according to claim 1, wherein a maximum-value holding device (13) is provided in the morphology detector (3), which incorporates a comparing device (14) and memory (15) in such a way that the comparing device (14) compares a respective current value (w2) of the signal width to a previous value (w1) of the signal width stored in memory (15) and, if the previous signal width value (w1) is exceeded, overwrites same with the current signal width value (w2), and that the maximum signal width value (w2) determined and stored in this manner can be compared by means of the comparator to the pre-set selection parameter for the purpose of discriminating between different types of tachycardia.

3. A cardioverter according to claim 1 with a morphology detector, wherein a peak value indicator (16) for the EKG signal, in such a way that a signal width value (w2) of the EKG signal measured by the signal width detector (10) can be used to distinguish between different types of tachycardia only if the EKG signal's peak value (a2) corresponding to the respective signal width value (w2) exceeds the preceding peak value (a1) of the EKG signal.

4. A cardioverter according to claim 1, wherein the morphology detector (3) can be deactivated during a predefinable refractory period of the heart.

5. A cardioverter according to claim 1, wherein the morphology detector (3), as a secondary detector, is hierarchically subordinate to a heart rate detector (4) of the cardioverter (2).

6. A cardioverter according to claim 1, wherein the morphology detector (3) detects the width of the signal pulses of the atrial and/or ventricular depolarization wave complex of the EKG signal.

7. A cardioverter according to claim 1 wherein the defined threshold value differs from the isoelectrical line by a finite amount.

\* \* \* \* \*